US012239356B2

(12) United States Patent
Fritz

(10) Patent No.: US 12,239,356 B2
(45) Date of Patent: Mar. 4, 2025

(54) APPARATUS FOR SUPPLYING A MEDICAL INSTRUMENT AND METHOD FOR MONITORING AN INSTRUMENT

(71) Applicant: ERBE ELEKTROMEDIZIN GMBH, Tuebingen (DE)

(72) Inventor: Martin Georg Fritz, Tuebingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 179 days.

(21) Appl. No.: 18/138,961

(22) Filed: Apr. 25, 2023

(65) Prior Publication Data

US 2023/0255675 A1 Aug. 17, 2023

Related U.S. Application Data

(63) Continuation of application No. 16/562,015, filed on Sep. 5, 2019, now Pat. No. 11,666,371.

(30) Foreign Application Priority Data

Sep. 7, 2018 (EP) ..................................... 18193140

(51) Int. Cl.
*A61B 18/12* (2006.01)
*A61B 18/02* (2006.01)
(Continued)

(52) U.S. Cl.
CPC .............. *A61B 18/10* (2013.01); *A61B 18/02* (2013.01); *A61B 18/1206* (2013.01);
(Continued)

(58) Field of Classification Search
CPC ......... A61B 18/02; A61B 18/10; A61B 18/14; A61B 18/1206; A61B 2018/00595; A61B 2018/00779; A61B 2018/00839; A61B 2018/00916; A61B 2018/00994; A61B 2018/0262; A61B 2018/1253; A61B 2018/126

See application file for complete search history.

(56) References Cited

U.S. PATENT DOCUMENTS 5,129,396 A 7/1992 Rosen
5,817,093 A 10/1998 Williamson, IV
(Continued)

FOREIGN PATENT DOCUMENTS

CN 105491958 A 4/2016
CN 106999148 A 8/2017
(Continued)

OTHER PUBLICATIONS

P. Laugier, et al., "A New Echographic Cryoprobe for In Vivo Ultrasonic Monitoring of Skin Cryosurgery", 1998 IEEE Ultrasonics Symposium Proceedings Oct. 1998, pp. 1337-1340.

*Primary Examiner* — Daniel W Fowler
(74) *Attorney, Agent, or Firm* — Blank Rome LLP

(57) ABSTRACT

An apparatus and method for sending test signals to an instrument, and checking the resultant and subsequently arriving echo signals in order to detect specific properties and changes of properties on the line, the instrument, the tissue or also on a fluid body, e.g., plasma body, present on an electrode of the instrument, and to control the operation of the supply arrangement accordingly.

19 Claims, 3 Drawing Sheets

(51) Int. Cl.
*A61B 18/10* (2006.01)
*A61B 17/00* (2006.01)
*A61B 18/00* (2006.01)
*A61B 18/14* (2006.01)

(52) U.S. Cl.
CPC ............... *A61B 2017/00022* (2013.01); *A61B 2018/00779* (2013.01); *A61B 2018/126* (2013.01); *A61B 18/14* (2013.01)

(56) References Cited

U.S. PATENT DOCUMENTS

| | | | |
|---|---|---|---|
| 5,991,142 | A | 11/1999 | Appelbaum |
| 6,235,018 | B1 | 5/2001 | LePivert |
| 8,968,303 | B2 | 3/2015 | Schall et al. |
| 9,125,658 | B2 | 9/2015 | Schall |
| 9,453,910 | B2 | 9/2016 | Elwart |
| 10,307,136 | B2 | 6/2019 | Deladi |
| 2005/0149012 | A1 | 7/2005 | Penny |
| 2006/0052777 | A1 | 3/2006 | Dumbauld |
| 2008/0183251 | A1 | 7/2008 | Azar |
| 2008/0234574 | A1 | 9/2008 | Hancock |
| 2009/0099561 | A1* | 4/2009 | McGreevy ......... A61B 18/1442 606/34 |
| 2011/0218491 | A1* | 9/2011 | Hauck ............... A61M 25/0147 604/95.04 |
| 2012/0203100 | A1 | 8/2012 | Weiss |
| 2013/0041361 | A1 | 2/2013 | Keller |
| 2015/0088039 | A1 | 3/2015 | Yon |
| 2015/0141847 | A1 | 5/2015 | Sarvazyan |
| 2017/0311922 | A1 | 11/2017 | Shan et al. |

FOREIGN PATENT DOCUMENTS

| | | |
|---|---|---|
| DE | 19961744 A1 | 6/2001 |
| EP | 1064532 A1 | 1/2001 |
| EP | 1064532 B1 | 3/2010 |
| EP | 2520241 B1 | 10/2016 |
| EP | 2520240 B1 | 1/2017 |
| RU | 2549314 C2 | 4/2015 |
| RU | 2015115118 A | 11/2016 |
| SU | 1681848 A1 | 10/1991 |
| WO | WO-99/47907 A1 | 9/1999 |
| WO | WO-2012/017731 A1 | 2/2012 |

\* cited by examiner

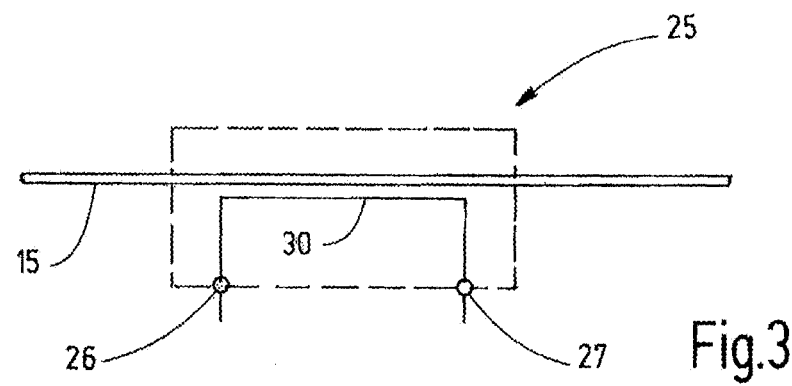
Fig.3
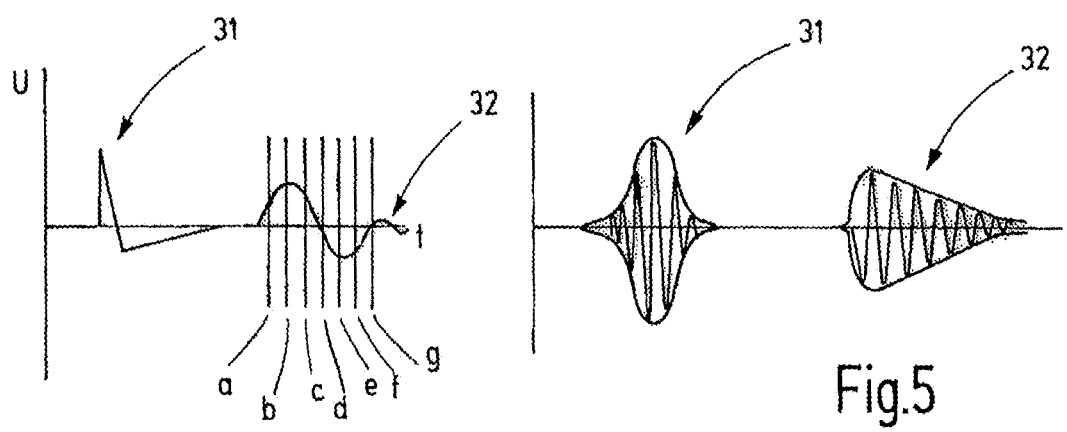
Fig.4
Fig.5
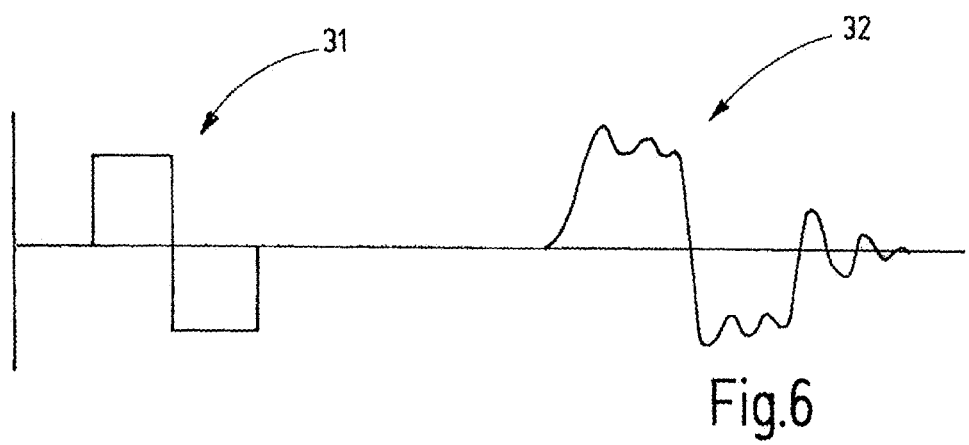
Fig.6

APPARATUS FOR SUPPLYING A MEDICAL INSTRUMENT AND METHOD FOR MONITORING AN INSTRUMENT

CROSS-REFERENCE TO RELATED APPLICATION

This patent application is a continuation application of U.S. patent application Ser. No. 16/562,015, filed on Sep. 5, 2019, which claims priority to European Patent Application No. 18193140.3, filed on Sep. 7, 2018. The contents of these applications are incorporated herein by reference in their entireties.

TECHNICAL FIELD

Embodiments of the invention described herein relate to an apparatus for supplying a medical instrument with signal power or operating power and/or with an operating medium, said medical instrument being connected to said apparatus via a line, as well as to a method for monitoring a medical instrument supplied by the apparatus via said line.

BACKGROUND

From publication EP 2 520 241 B1 an arrangement comprising a medical instrument for the treatment of a patient and an apparatus for supplying the instrument with treatment current has been known. During treatment, the apparatus measures the electrical current flowing through the tissue of the patient as well as an electrical voltage applied to the instrument and utilizes the obtained current and voltages values for the control of the apparatus.

Using a slightly different control algorithm, the device according to publication EP 2 520 240 B1 also uses the current passed by an instrument through biological tissue, as well as the voltage applied to the tissue and the instrument, respectively, for control of the apparatus.

Publication EP 1 064 532 B1 discloses a method for measuring the blood coagulation time of a blood sample of a patient, wherein the blood in a testing chamber is charged via electrical contacts with test signals of a voltage generator so that a current flows through the blood, said current changing consistent with the blood coagulation.

Said arrangements and methods are individually specifically set up for specific measurements on biological tissues.

It is the object of embodiments of the invention to provide a concept for the electrical monitoring of medical instruments, as well as their associate components and the operation of same.

The concept according to embodiments of the invention is implemented in an apparatus for supplying a medical instrument connected to the apparatus via a line with signals or operating power and/or an operating medium, wherein a test pulse emitter is provided, said test pulse emitter being adapted to emit test signals to the line connecting the apparatus to the instrument. Furthermore, the apparatus comprises an echo receiver that is adapted to receive the echo signal coming back via the line in response to the test signal. The echo signal is fed to an analysis device that is disposed to detect the physical state in or on the instrument and/or in or on the line with the use of the echo signal. The test signal is preferably free of dc voltages and, depending on the application, may display a peak voltage of a few Volts up to several 1000 Volts.

The line may be a fluid line, in particular a metal capillary or a fluid tube that contains one or more electrical conductors or that itself is an electrical conductor. The test signal output to the line supplied by the test signal emitter then moves on or in the line to the instrument and is completely or partially absorbed and/or completely or partially reflected by said instrument. Corresponding to its propagation delay, the reflected echo signal arrives with a delay on the echo signal receiver and is then passed by said receiver on to the analyzing device. Now the analyzing device can use the propagation delay, as well as the signal deformation (distortion) or any other properties of the echo signal such as, e.g., phase shift, amplitude, envelope curve and the like, can draw conclusions regarding the status of the line (e.g., its length or integrity, the physical state in or on the instrument, for example the activation of an activating switch, the contact relative to the biological tissue or the condition of same, whereupon the apparatus can be controlled accordingly. For example, the instrument may be a cryosurgical instrument, in which the test signal moves up to the cryotip and is reflected thereby back to the apparatus. At the start of glaciation on the cryotip, characteristic parameters of the echo signals change, for example regarding their phase shift, so that the start of glaciation can be recognized and the glaciation time from the start of glaciation can be calculated. The formation of ice in or on the line may also affect the echo signal. For example, multiple echos may form and their presence may be utilized as a criterion for generating a corresponding signal indicating the event. Other applications are possible. For example, with the application an autostart detection—i.e., an automatic treatment is possible in the case of cryosurgical instruments, as well as in the case of electrical instruments—as a function of the defined conditions on the instrument. Also, in the case of electrical instruments, an early spark detection, plasma monitoring, ionization detection or ionization measurement can be performed.

The instrument may also be an electrosurgical bipolar or monopolar instrument that is connected to the apparatus that provides the supply. To accomplish supplying, the apparatus may contain a voltage-generating generator, e.g., an HF-generator, which delivers a voltage of typical close to or above 100 V or also substantially higher. Typically, the treatment current may be provided pulsed, e.g., as a pulse width modulated signal, in which case the test signal emitter preferably emits at least one test signal respectively during pauses of the pulsed treatment current. The pauses between the treatment current pulses are preferably longer than the propagation delay between the emission of a test signal and the arrival of the echo signal. Preferably, the pauses are longer than a multiple of the propagation delay of the test signal.

The echo signal may be dependent on the physical conditions on the instrument such as, for example, the condition and/or the temperature of an electrode, the electrical capacitance of the electrode relative to the patient or to the counter-electrode, an electrical resistance between the electrode and the counter-electrode, the electrical inductivity of the signal path, an electrical impedance, a conductivity of a fluid existing on the electrode, in particular a gas, the contact of the line with another body or object and the like.

The physical conditions may have an effect on the properties of the echo signal. Such properties may be, for example, the propagation delay, the number of echo signals, the echo signal amplitude, the distortion of the test signal (i.e., its waveform) or the phase shift of the echo signal compared with the test signal, the presence or disappearance of the echo signal.

The apparatus may comprise a control device that responds to at least one or more of these detected physical conditions with an action such as, for example, switching the generator on and off, the increase or decrease of the generator power, the peak voltage of the treatment current, the pulse duration of the treatment current or the pauses between individual treatment current pulses or the like. The actions that trigger a response to a characteristic change of the echo signal may also include the activation or deactivation of the instrument and/or the supplying apparatus. The activation or deactivation of the supplying apparatus means the clearing or blocking of the operating power or the operating medium.

The test signal emitter is preferably disposed to generate test signals that are free of dc voltages and/or dc currents. Such test signals are, for example, modulated HF-signals, e.g., having a bell-shaped envelope curve, wherein the duration of such a test signal is preferably a few nanoseconds. Such a signal having a bell-shaped envelope curve may be a radio-frequency signal burst and is viewed as a signal test signal pulse. However, it is also possible, to use differently modulated HF-signals or pulse signals as test signals, for example in particular pulse signals free of dc voltages of the type of Dirac pulses, triangular pulses, sawtooth pulses, rectangular pulses, sinc pulses or pulses approaching such pulses. Sinc pulses are understood as to refer to pulses having the form (sin x)/x or pulses that are derived from one or more such pulses.

By introducing test pulses into the line and outputting echo signals preferably by inductive and/or capacitive coupling of the electrical measuring circuit to the line, e.g., via directional couplers, the electronic control system and the patient electrical circuit are galvanically separated.

The method according to embodiments of the invention is disposed for monitoring a medical instrument that is supplied by the apparatus via line, wherein at least one test signal is delivered to the line connecting the apparatus to the instrument, the echo signal coming back via the same line is received and then subjected to an analysis, wherein-based on the analysis-a change of a physical condition in or on the instrument, as well as optionally also in or on the line supplying the instrument, is detected. By analyzing the properties of the echo signal arriving at a time offset relative to the emission of the test signal it is possible to monitor the function and the condition of the line, as well as the instrument and, in addition, the biological tissue influenced by the instrument.

BRIEF DESCRIPTION OF THE DRAWINGS

Additional details of advantageous embodiments are the subject matter of the description, the claims or the drawings. They show in FIG. 1 a schematic representation of an arrangement for the cryogenic treatment of a patient with a cryosurgical instrument and an apparatus for supplying said apparatus, FIG. 2 a schematic representation of the cryosurgical instrument and biological tissue that is influenced thereby, FIG. 3 a schematic representation of a directional couple for outputting an echo signal from the line supplying the instrument, FIGS. 4-6 schematic diagrams of various test signals and their echos, FIG. 7 a schematic representation of an arrangement for the electrosurgical treatment of biological tissue with the use of a bipolar instrument and an apparatus supplying said instrument, and FIG. 8 a directional coupler for outputting the echo signal from a line supplying the instrument.

DETAILED DESCRIPTION

Figure 1:
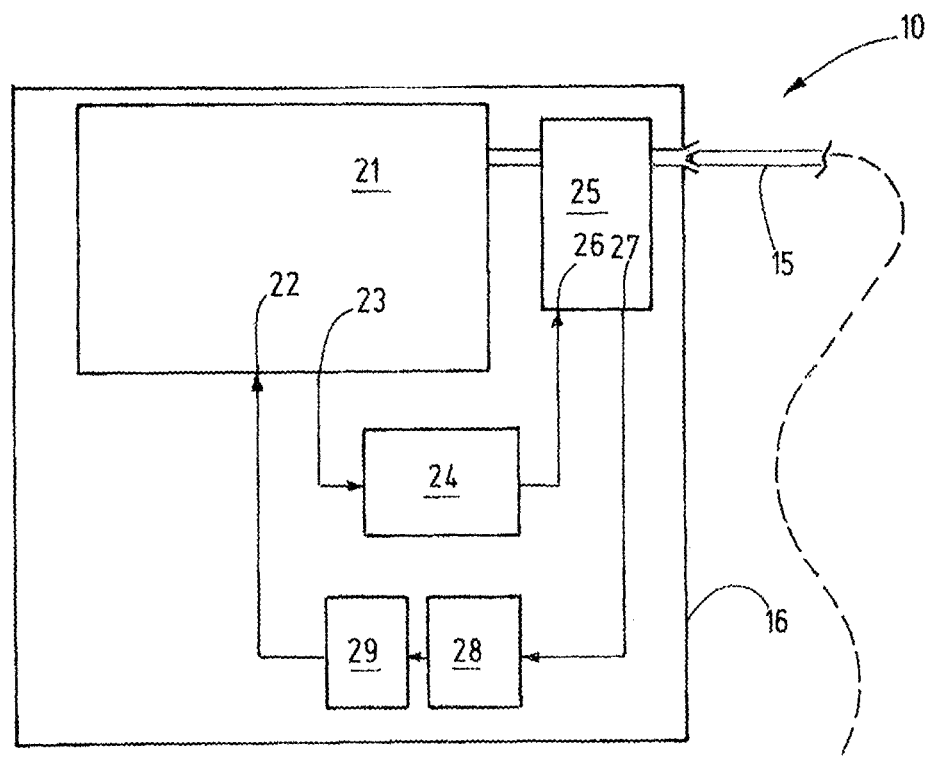

FIG. 1 shows a cryosurgical arrangement 10 that is disposed to act on a patient. In FIG. 1 he/she is lying strictly in an exemplary manner on a table 12 via which the patient 11 is connected at least in a capacitive manner to the ground potential 13.

A cryoprobe 14 is used for the treatment of the patient 11, said cryoprobe being connected to a supplying apparatus 16 via a line 15. Typically, the line 15 is a fluid line, for example a capillary tube, a hose or the like. Via the line 15, a treatment fluid is conveyed by the apparatus 16 to the instrument 14. As can be inferred from FIG. 2, the line 15 may comprise a supply line 17 as well as a return line 18. Preferably, at least one of the two lines 17, 18 is configured so as to be electrically conductive or is provided with an electrical conductor, so that the cryotip 19 that is disposed for the direct contact with biological tissue 20 can be reached by an electrical test signal that-emitted by apparatus 16—travels via the line 15 to the instrument 14, in particular the cryotip 19, and from said tip via the line 15 back to the apparatus 16. Preferably, the test signal is shorter than its propagation delay, so that the test signal and the echo signal occur on the start of the line in a manner offset in view of time. The cryoprobe 19 can galvanically or also only capacitively couple with an electrical line contained in the line 15.

The apparatus 10 contains a supply arrangement 21, via which the instrument 14 is supplied with operating medium and/or operating power. In the exemplary embodiment according to FIG. 1 the operating medium is a fluid, for example carbon dioxide or laughing gas ($N_2O$), nitrogen, e.g. as gas or fluid, preferably close to the boiling point curve, or as a two-phase mixture. The supply arrangement 21 contains or is connected to an appropriate fluid supply. For manual control, in particular for triggering a treatment, i.e., for signaling the treatment start, a not specifically illustrated control input may be provided. Alternatively or additionally, the supply arrangement may comprise a control input 22, via which a switch-on or a switch-off signal or another control signal can be received. Furthermore, the supply arrangement 21 may comprise an output 23, via which said supply arrangement can send a query command to downstream arrangements. The query command may be disposed to trigger a measuring cycle that is defined to determine a physical condition in or on the line 15, as well as in or on the instrument 14. In the exemplary embodiment according to FIG. 1, a test signal emitter 24 is connected to the output 23, said test signal emitter delivering a test signal to the line 15 via a coupling arrangement 25. In this embodiment and all other subsequently described embodiments this test signal has a certain signal duration that is as long as or preferably shorter than the propagation delay of the test signal on line 15 to the instrument 14 and as echo signal back to the coupling arrangement 25.

In addition to a signal output 26, the coupling arrangement 25 has a signal input 27 that provides the echo signal conducted out on line 15 and transfers it to an echo signal receiver 28. Said receiver is part of or connected to an analysis device 29 that checks the echo signal and emits a control signal consistent with the test result to the control input 22.

FIG. 3 shows the coupling arrangement, schematically and as an example. The coupling arrangement 25 is a directional coupler for coupling and uncoupling electrical signals into line 15 that is electrically conductive and configured as a fluid line. To do so, a conductor section 30 is arranged on a suitable support, said conductor coupling capacitively-along the entire length or at least on its ends—with the line 15, while said conductor displays an inherent inductivity different from zero. The wave of an electrical signal, for example a test signal 21, moving forward and backward on line 15 can be tapped separately in each case. Preferably, the chronological length of this signal is shorter than the time that is required by the test signal 31 to move back as the echo 32 to the instrument 14 via the line 15. Typically, the test signal 31 has a length of a few nanoseconds FIG. 4 shows as the exemplary test signal a needle-shaped positive voltage pulse followed by a negative triangular pulse. The surface areas bordered by the positive and the negative part of the test signal preferably have the same dimension, so that the test signal 31 is overall free of any dc component.

The echo signal 32 has a changed form that is symbolically illustrated by FIG. 4. For example, high-frequency components may be missing while overshoots occur, in which case the echo signal may also be chronologically drawn out or compressed and its amplitude may have changed, in particular decreased.

Preferably, the echo signal receiver 28 is set up to repeatedly sample echo signals 32 originating from successive test signals 31 but in a chronologically offset manner. In FIG. 4, these sampling points are indicated symbolically by vertical lines a, b, c, d, e, f, g. Based on sampling values obtained at various times a to g, the echo signal receiver 28 constructs the echo signal. The number of samplings is defined consistent with the purpose. To this extend, FIG. 4 is simply exemplary.

Figure 2:
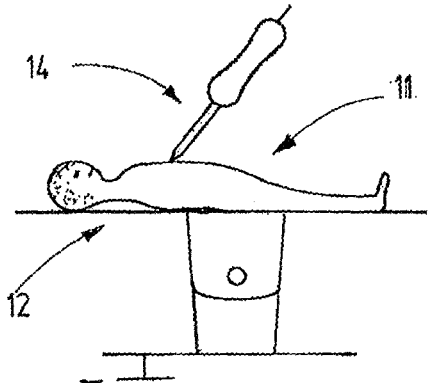
Figure 2:
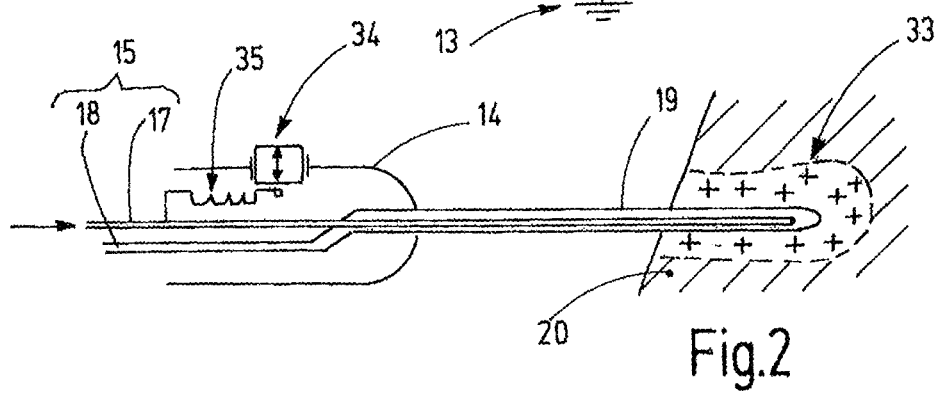

The arrangement 10 described so far works as follows:

Following the basic activation of the apparatus 16 and placing the instrument 14 on or in the tissue 20 of the patient 11, e.g. similar to FIG. 2, the supply arrangement 21 is cleared, so that it delivers fluid to the cryotip 19 via the line 15. Initially, the cryotip 19 is still surrounded by moist, living tissue. Previously or at the same time, the test signal emitter 24 is activated and now emits test signals 31, e.g., according to FIG. 4, to the coupling arrangement 25 and via the latter to the line 15. Now each test signal 31 moves along the line 15 to the tip 15, where it impinges on the at least capacitively grounded tissue 20. The electrically conductive tissue 20 thus closes the electric circuit comprising the line 15 and cryotip 19 in a capacitive and resistive manner. Accordingly, the test signal 31 is attenuated and, depending on the electrical resistance existing on the cryotip, reflected with the same or inverted phase. At the same time, said signal is distorted as a consequence of the capacitance and the inductance as well as the influence of the tissue 20, which is why the echo signal 32 has a different waveform than the test signal 31. After several successive measuring example in a few microseconds, said cycles consisting of the emission of a test signal 21 by the test signal embitter 24 and the reception of the echo signal by the echo signal receiver 28, the form of the echo signal 32 has been determined and can be analyzed by the analysis arrangement 29. With the continuous cooling of the cryotip 19, a frozen region 33 can form in the tissue 20, which region characteristically changes the physical properties in the immediate vicinity of the probe tip 19. For example, the current conductivity decreases. Thus, also the form of the echo signal 32 changes significantly. For example, the initial ice formation on the cryotip 19 may have the result that the end of the cryotip 19 viewed as the wave conductor acts as electrically "open", whereas it had to be viewed as "short-circuited" prior to the formation. Accordingly, the echo signal 32 changes its phasing at the onset of ice formation. This change in phasing can be detected by the analysis arrangement 29 and an appropriate signal can be delivered to the control input 22. The signal can be used for controlling the operation of the supply arrangement 21. To the extent that the supply arrangement 21 now provides a specifically defined time for the ice formation on the cryotip 19, the specified freezing time can now be started with the arrival of the signal at the control input 22.

The exemplary embodiment described hereinabove serves to provide the illustration of the principal. However, the analysis arrangement 29 can also be set up to perform substantially more sensitive analyses. For example, it is possible with the form of the echo signal 32 to detect one or more additional or other physical conditions such as, for example, the temperature of the cryoprobe 19 and/or the tissue 20, the size of the frozen tissue 33, the type of a cryotip 19 attached to the instrument 14, the length of the line 15 and the like.

Additional applications of the concept according to embodiments of the invention are possible. For example, the cryotip 19 may be electrically insulated from the fluid supply line 17 and thus also from the line 15. The same may be applicable for the fluid return line 18. In this case, the principle according to embodiments of the invention can be used to detect a change that has been manually caused on the instrument 14. For example, an electrically conductive control element 34 may be provided for this, which element can be brought in and out of engagement with the fluid supply line 17 or with the fluid return line 18 (or both), so that said element locally affects the capacitance of the line 15 or the cryotip. Furthermore, the control element 34 may be electrically conductive and that be galvanically connected to the operator, as soon as the operator touches said element. It can be connected to the line 15 or disconnected therefrom, depending on how an operator actuates the control element 34. If the control element 34 is electrically disconnected from the line 15, the echo signal 32 has a different form than in the in which it is connected to the line 15. The corresponding signal change can be used by the analysis arrangement 29 to switch the supply arrangement 21 on and off.

The last described embodiment with control element 34 can also be combined with the previously described embodiment, wherein the cryotip 19 is electrically connected to line 15. For example, multiple echos occurring during the actuation of the control element can be used as an indicator for the confirmation of the control element 34.

It is also possible to interpose, between the control element 34 and the line 15, another element such as, for example, an inductance 35 or, as indicated in FIG. 2, a parallel oscillating circuit, a series oscillating circuit or the like. The elements or oscillating circuits may affect the test signal in an individually characteristic manner and, accordingly, cause characteristic echo signals.

If several such oscillating circuits or other electrical elements and several control elements are arranged on the instrument 14, various commands can be transmitted to the supply arrangements via the various changes of the echo signal 32 that can be achieved therewith.

It is true of all previously and subsequently described embodiments that they can be operated with the test signal 31 according to FIG. 4, as well as, alternatively, also with other test signals such as are illustrated strictly as examples in FIGS. 5 and 6. An advantageous test signal is understood to mean an HF-signal that has been amplitude-modulated with a Gauss curve, as illustrated by FIG. 5. It is free of any dc voltage component.

Instead of an amplitude-modulated HF-signal, it is also possible to use a sinc signal that is provided as a single pulse or also as a sequence of two or more sinc pulses having different polarities.

The echo signal 32 according to FIG. 4 typically has a changed envelope curve that is characteristic of various physical conditions on the instrument 14. In doing so, the physical conditions may be the influenced biological tissue 20, as well as other conditions, such as, for example, the contact or actuation of one control element 34 (or additional control elements. In addition to the envelope curve, it is also possible to analyze the phase position of the HF oscillation modulated by the envelope curve. All of these variations represent possible embodiments of the echo signal receiver 28 and the analysis arrangement 29.

FIG. 6 shows another possible test signal, for example having the configuration of a positive rectangular signal and a subsequent—with a pause or directly-negative rectangular pulse. The associate echo signal 23 may display a reduced flank steepness, overshoots, a phase shift and further such changes relative to the test signal 31. Each change of the echo signal 32 compared with the test signal 31 can be understood as a characteristic for a change of the physical conditions occurring on the line 15 and/or the instrument 14 and be appropriately evaluated by the analysis arrangement 29.

Instead of the rectangular pulses according to FIG. 6, it is also possible to use triangular or trapezoidal pulses as the test signal 31. Additional signal forms are possible.

Figure 7:
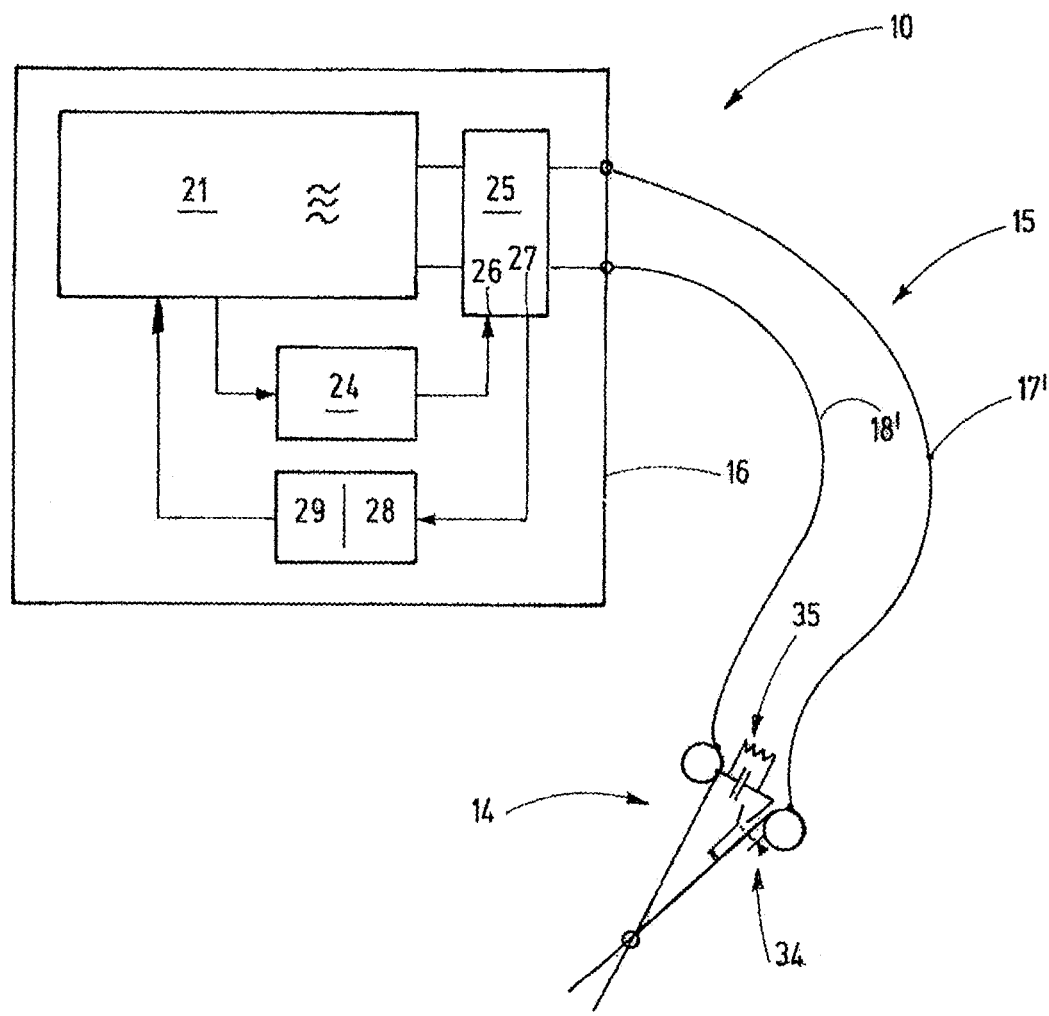

The principle according to embodiments of the invention is basically suitable for all arrangements 10, wherein an apparatus 16 supplies a monopolar or bipolar instrument 14 with a medium or also with an operating power, for example electrical current or electrical voltage. For illustration, FIG. 7 shows a bipolar instrument 14 with the supply arrangement 21 being an HE-generator. The instrument 14 is symbolically shown as a cauterization forceps, wherein each design of a bipolar electrical instrument 14 may be used. The line 15 comprises an electrical supply line 17' and an electrical return line 18' that, together, form a waveguide. For example, the lines 17', 18' are connected to the two branches of the cauterization forceps. In addition, a control element 34, for example in the form of an electrical switch, may be provided, with which the lines 17', 18' can be connected to each other via an element that is able to change the waveguide properties of the line 15. For example, the element may have an inductance 35 or, as shown, be an oscillation circuit. The oscillation circuit may be a parallel circuit, a series circuit or a component that combines capacitive, as well as inductive, properties. Alternatively, a resistive element may be provided, for example a resistor that corresponds to the wave resistance of the line 15. In this case, a closing of the switch 34 causes an absorption of the test signal 31 so that the echo signal 32 is not necessary.

Figure 8:
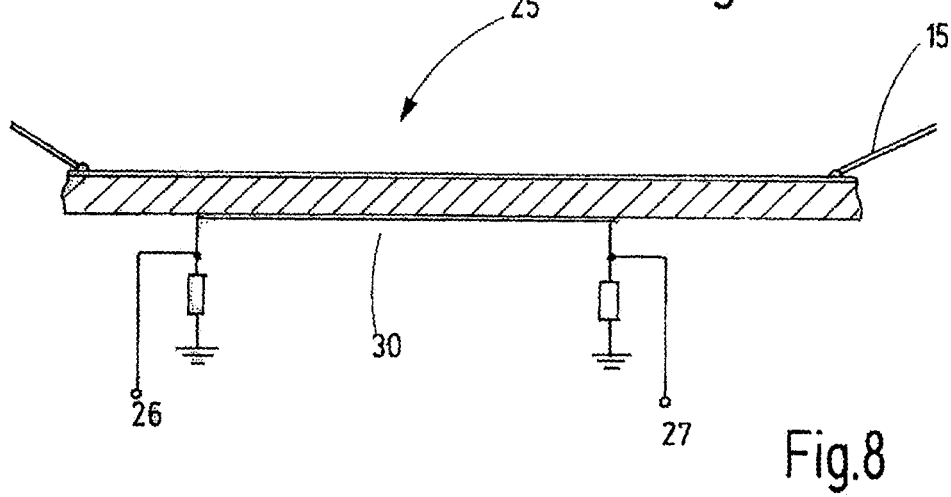

The coupling arrangement 25 according to FIG. 8 may be a directional coupler that, for example, is configured as a coaxial arrangement or as a conductor strip on a circuit board. For example, the line 15 conducting the treatment current can be arranged on one side of the circuit board, while the conductor section 30 is arranged on the opposite side thereof. Thus, it is possible in a simple manner to achieve a high electrical insulation resistance and thus a safe separation between the electrical circuit leading from the electrical generator of the supply arrangement 21 to the instrument 14 and the test signal circuit leading from the test signal emitter 24 to the test signal receiver 28.

Again, it is possible to implement numerous variants with the arrangement 10. For example, the analysis arrangement 29 can detect—by suitable evaluation of the echo signal 32—the start and the end of a cauterization or also a successful severing of tissue, as well as an actuation of a potentially available control element 34.

The principle can also be applied to monopolar instruments, wherein only the supply line 17' leads f from the apparatus 16 to the instrument 14, while the return line 18' leads from a neutral electrode fastened to the patient to the apparatus 16. Also in this case the test signal 31 moves-via the supply line 17'—from the apparatus 16 to the instrument 14, and the echo signal 32 moves on the same supply line 17' from the instrument 14 back to the generator 16. Again, the change of the echo signal 32 compared with the test signal 31 is an indicator of the physical conditions on the supply line 17' and on the instrument 14, so that corresponding changes of the echo signal can be used for triggering actions such as, for example, switching the supply arrangement on and off, increasing or minimizing the voltage, power or current of the latter, and/or the change of the signal form of the voltage output by the supply arrangement 21.

In the case of all the arrangements 10 wherein the supply arrangement 21 is disposed for the delivery of an electrical treatment current, the emission of test signals 31 with the receipt of the echo signals 32, preferably during short pauses during which the supply arrangement 21 does not output a power signal to the line 15. To accomplish this, the operator of the generator of the supply arrangement 21 is preferably repetitively interrupted shortly. For example, the generator is an HF-generator that oscillates with a base frequency of several 100 Hz (e.g.) 350 or 400 Hz), wherein it is pulse width modulated with a frequency of several kHz (e.g., 46 kHz). In doing so, the HF-signal output by the generator is subjected to rectangle modulation, for example, i.e., a sequence of successive HF-oscillation packages. Each HF-oscillation package consists of at least one, optionally also more or many HF-oscillations. The emission of the test signal 21 and the receipt of the echo signal 32 preferably occurs in the pauses between two successive HF-oscillation packages.

With the introduced concept it is not only possible to determine properties of the instrument 14 and properties of the tissue 20, but also properties of an electrode of the fluids surrounding the instrument, in particular gases or plasmas. For example, in the case of an instrument working with spark discharge, it is to determine the state of ionization of the gas present on the electrode by means of test pulses during the pauses between two HF-oscillation packages and to use this for an operation of the supply arrangement 21. The test pulses may have voltage amplitudes of above 1000 V. For example, on a monopolar or bipolar coagulation instrument the pause can be reduced between two successive HF-oscillation packages when-during the pause between two successive HF-oscillation packages, a recombination of the plasma that has gone too far is detected. Also, the electrode temperature can have an influence on the form of the echo signal 32 and can thus be determined via an evaluation of the echo signal.

On the other hand should a new ignition be desired with each HF-oscillation burst, the distance between individual bursts can be increased until a sufficient recombination of the plasma has been detected.

Furthermore, it is possible with the pulse echo measurement to detect subtle dynamic changes of the conditions on an electrode during a treatment operation and use them to control the supply arrangement 21. For example, in the case of the contact coagulation, the electrode of the instruments may initially be brought into contact with moist tissue. In this state, the echo signal 32 has a characteristic form. As soon as due to the continued energy application of the involved electrode a drying of the electrode and vapor formation on the tissue is noted, the echo signal 32 changes its form in a characteristic manner. The supply arrangement 21 can now change its energy output, e.g., reduce the voltage, in order to prevent a now threatening spark formation, for example. The peak voltage and/or the duty cycle or other influencing factors can be changed, e.g., decreased. Inasmuch as the form of the echo signal responds to the conditions on the electrode in a highly sensitive manner, each desired operating mode, e.g., the contact coagulation, can be implemented with continuous control engagement and thus maximize the energy input, without risking a spark formation. On the other hand, considering treatment modes wherein the spark formation is desired, it is possible by continually monitoring the form of the echo signals to achieve a desired operating mode, for example the spark formation and the plasma creation with a pulse width modulated HF-signal under different premises, for example minimum power or maximum cutting effect or the like.

With the apparatus according to embodiments of the invention and with the method according to embodiments of the invention test signals 31 are transmitted by an apparatus 16 to an instrument 14 and the resultant and subsequently arriving echo signals 32 are checked in order to detect specific properties and changes of properties on the line 15, the instrument 14, the tissue 20 or also on a fluid body, e.g., plasma body, present on an electrode of the instrument 14, and to control the operation of the supply arrangement 21 accordingly.

The invention claimed is:

1. An apparatus for supplying at least one of an operating power and an operating medium via a line to a medical instrument for treating tissue, the apparatus comprising:
    a test signal emitter adapted to deliver successive test signals to the line, the successive test signals having a first shape;
    an echo signal receiver adapted to receive successive echo signals caused by the test signals, the successive echo signals having a second shape different than the first shape, wherein the second shape is an envelope curve; and
    an analysis arrangement adapted to detect, based on the change in the envelope curve of the echo signal, a length of the line.

2. The apparatus of claim 1, wherein the line is a fluid line and the operating medium is a fluid.

3. The apparatus of claim 1, wherein the line is an electrical line and the operating power comprises a treatment current, and wherein the electrical line is connected to a source for supplying the treatment current.

4. The apparatus of claim 3, wherein the source is a supply arrangement adapted to provide the treatment current in a pulsed manner and wherein the test signal emitter is active during pauses of the treatment current.

5. The apparatus of claim 3, wherein the analysis arrangement is further adapted to detect, based on the change in the envelope curve of the echo signal, a physical condition selected from one or more of a temperature, a moisture, an electrical capacitance, an electrical resistance, an electrical inductance, an electrical impedance, a resonance property, a propagation delay, a number of reflections, an echo signal amplitude, a distortion, a phase position or a polarity.

6. The apparatus of claim 1, wherein the analysis arrangement is adapted to trigger an action in response to a characteristic change of the echo signal.

7. The apparatus of claim 6, wherein the action comprises an activation or deactivation of the instrument.

8. The apparatus of claim 6, wherein the action comprises generation of a signal that denotes a connected instrument.

9. The apparatus of claim 1, wherein the test signal emitter is adapted to generate test signals free of any dc voltage and/or dc current.

10. The apparatus of claim 1, wherein the test signal emitter is adapted to emit a first shape having a needle-shaped positive voltage pulse followed by a negative triangular pulse.

11. A method for operating an apparatus to monitor a medical instrument for treating tissue and connected to the apparatus via a line, the method comprising:
    supplying at least one of an operating power and an operating medium to the instrument via the line;
    delivering at least first and second test signals to the line;
    receiving at least first and second echo signals having respective first and second envelope curves caused by the first and second test signals, the first and second envelope curves being different from one another;
    analyzing the change in the first and second envelope curves from respective first and second echo signals; and
    detecting a length of the line based on the change of the first and second envelope curves.

12. The method of claim 11, wherein the test signals comprise dc voltage free and/or dc current free pulses.

13. The method of claim 11, wherein the method is performed when the instrument is used on a human or animal body.

14. The method of claim 11, further comprising:
    controlling at least one of the apparatus and the instrument based on a characteristic change of the change in the first and second envelope curves from respective first and second echo signals.

15. The apparatus of claim 1, wherein the analysis arrangement is further adapted to detect, based on the change in the first and second envelope curves from respective first and second echo signals, a change of a physical condition in or on the line.

16. The method of claim 11, further comprising:
    detecting a change of a physical condition in or on the line based on the analysis.

17. The apparatus of claim 16, wherein the change in physical condition comprises a frozen region forming in the tissue.

18. The apparatus of claim 16, wherein the change in physical condition comprises the size of a frozen region forming in a portion of the tissue located at a distal tip of the medical instrument.

19. The method of claim 11, wherein the detecting step includes detecting a change in both amplitude and frequency between the first and second envelope curves.

* * * * *